US010053722B2

(12) United States Patent
Ménard et al.

(10) Patent No.: US 10,053,722 B2
(45) Date of Patent: Aug. 21, 2018

(54) ENRICHMENT AND ISOLATION OF MICROBIAL CELLS AND MICROBIAL NUCLEIC ACIDS FROM A BIOLOGICAL SAMPLE

(71) Applicant: Geneohm Sciences Canada Inc., Québec (CA)

(72) Inventors: Christian Ménard, St-Lambert-de-Lauzon (CA); Annie Roy, Québec (CA); Patrick Boucher, Québec (CA); Steve Létourneau, St-Romuald (CA)

(73) Assignee: Geneohm Sciences Canada Inc., Quebec (CA)

( * ) Notice: Subject to any disclaimer, the term of this patent is extended or adjusted under 35 U.S.C. 154(b) by 260 days.

(21) Appl. No.: 14/367,662

(22) PCT Filed: Dec. 20, 2012

(86) PCT No.: PCT/CA2012/050922
§ 371 (c)(1),
(2) Date: Jun. 20, 2014

(87) PCT Pub. No.: WO2013/091102
PCT Pub. Date: Jun. 27, 2013

(65) Prior Publication Data
US 2014/0335522 A1 Nov. 13, 2014

Related U.S. Application Data

(60) Provisional application No. 61/578,352, filed on Dec. 21, 2011.

(51) Int. Cl.
*C12Q 1/28* (2006.01)
*C12Q 1/6806* (2018.01)
*C12N 1/06* (2006.01)
*C12N 15/10* (2006.01)
*C12Q 1/24* (2006.01)

(52) U.S. Cl.
CPC .............. *C12Q 1/6806* (2013.01); *C12N 1/06* (2013.01); *C12N 15/1003* (2013.01); *C12Q 1/24* (2013.01)

(58) Field of Classification Search
None
See application file for complete search history.

(56) References Cited

U.S. PATENT DOCUMENTS

| 7,494,771 | B2 | 2/2009 | Picard et al. | |
|---|---|---|---|---|
| 2008/0160528 | A1 | 7/2008 | Lorenz | |
| 2008/0300396 | A1* | 12/2008 | Deggerdal | C12N 15/1006 536/25.41 |
| 2012/0231446 | A1 | 9/2012 | Heckel et al. | |

FOREIGN PATENT DOCUMENTS

| DE | 102005009479 A | 9/2006 |
|---|---|---|
| EP | 0745849 A2 | 12/1996 |
| EP | 2325312 | 5/2011 |
| WO | WO 2009/015484 | 2/2009 |
| WO | WO 2010/062354 | 6/2010 |
| WO | WO 2011/070507 | 6/2011 |
| WO | WO 2012/168003 | 12/2012 |
| WO | WO 2013/130759 | 9/2013 |

OTHER PUBLICATIONS

Applied Biosystems Ambion, Catalog #: AM9820-AM9823, Feb. 1, 2008, 1 page.*
COLD Spring Harbor Protocols, "SDS (10%) stock solution", 2006, Retrieved from the Internet: URL: http://cshprotocols.cshlp.org/content/2006/1/pdb.rec10480.full?text_only=true [retrieved on Jul. 9, 2015], 1 page.
Ecker et al., "The Microbial Rosetta Stone Database: A compilation of global and emerging infectious microorganisms and bioterrorist threat agents", BMC Microbiology (2005) 5: 19; 17 pages.
Jonsson et al., Theoretical aspects of detection of bacteraemia as a function of the volume of blood cultured, APMIS (1993) 101(8): 595-601.
Loonen et al., "Comparison of Pathogen DNA Isolation Methods from Large Volumes of Whole Blood to Improve Molecular Diagnosis of Bloodstream Infections" PLos One (Aug. 2013) 8(8): e72349.
Restrepo et al., "Selective enrichment and detection of mycobacterial DNA in paucibacillary specimens", J Microbiol Methods (2006) 67(2): 220-229.
Kok et al., "Identification of Bacteria in Blood Culture Broths Using Matrix-Assisted Laser Desorption-Ionization Sepsityper™ and Time of Flight Mass Spectrometry", (Aug. 2011) 6(8): e23285; 7 pages.
Vaught, J.B., "Blood Collection, Shipment, Processing, and Storage", Cancer Epidemiol Biomarkers Prev. (2006) 15(9): 1582-1584.
White et al., "The Evolution and Evaluation of a Whole Blood Polymerase Chain Reaction Assay for the Detection of Invasive Aspergillosis in Hematology Patients in a Routine Clinical Setting", Clin Infect Dis. (2006) 42(4): 479-486.
Wiesinger-Mayr et al., "Establishment of a semi-automated pathogen DNA isolation from whole blood and comparison with commercially available kits", J Microbiol Methods (Jun. 2011) 85(3): 206-213.

(Continued)

*Primary Examiner* — Kade Ariani
(74) *Attorney, Agent, or Firm* — Knobbe, Martens, Olson & Bear, LLP

(57) ABSTRACT

A method for enrichment and isolation of microbial cells and microbial nucleic acids from a biological sample is described. The method comprises (i) adding to an initial volume of biological sample a differential cell lysis solution to obtain a final concentration of 0.1 to 1% of SDS in the sample; (ii) mixing the solution obtained in step (i) for a period of time sufficient to lyse the host cells present in the biological sample, while preserving the integrity of cells; and (iii) separating the microbial cells from the lysed host cells components. Differential cell lysis solutions and kits for practicing the method of the present invention are also provided.

17 Claims, 7 Drawing Sheets

(56) References Cited

OTHER PUBLICATIONS

International Search Report and Written Opinion dated Mar. 8, 2013 in Application No. PCT/CA2012/050922, filed Dec. 20, 2012.
European Supplemental Search Report dated Jul. 20, 2015 in Application No. 12860922.9, filed Jun. 19, 2014.
Rossmanith et al., Development of matrix lysis for concentration of gram positive bacteria from food and blood. J Microbiol Meth. (2007) 69: 504-511.
European Office Action dated Nov. 9, 2016 in Application No. 12860922.9, filed Jun. 19, 2014.

* cited by examiner

ENRICHMENT AND ISOLATION OF MICROBIAL CELLS AND MICROBIAL NUCLEIC ACIDS FROM A BIOLOGICAL SAMPLE

CROSS REFERENCE TO RELATED APPLICATIONS

This application is a national phase entry under 35 U.S.C. § 371 of International Application No. PCT/CA 2012/050922, filed on Dec. 20, 2012, published in English, which claims priority from U.S. provisional application Ser. No. 61/578,352, filed on Dec. 21, 2011, the disclosures of which are incorporated herein by reference.

STATEMENT REGARDING FEDERALLY SPONSORED RESEARCH OR DEVELOPMENT

N.A.

FIELD OF THE INVENTION

The present invention relates to methods for preparing biological samples for analysis. More particularly, the present invention relates to processing of biological samples for enrichment and isolation of microbial cells and their nucleic acids for subsequent analysis, including for example, nucleic acid amplification. The present invention also relates to the detection of microbial cells in biological samples.

REFERENCE TO SEQUENCE LISTING

The instant application contains a Sequence Listing which has been submitted in ASCII format via EFS-Web and is hereby incorporated by reference in its entirety. Said ASCII copy, created on Dec. 17, 2012 and modified on Jun. 20, 2014, is named 787-Sequence listing_ST25.txt and is 1,005 bytes in size.

BACKGROUND OF THE INVENTION

The isolation and purification of microorganisms and their nucleic acids from biological materials represent a fundamental technique for molecular-biological analysis and diagnosis in human or veterinary medicine. Infections need to be detected quickly and reliably, to ensure that appropriate therapy is undertaken without delay.

Many biological samples and materials of interest contain substances that reduce the efficiency of nucleic acid testings. For example, it is well known that many substances that inhibit enzyme activity are present in many types of cells and can limit the use of amplification assays such as PCR. For example, heme, the oxygen carrier in blood, as well as its derivatives, can inhibit PCR amplification of target DNA in samples containing blood. Heme's breakdown products, such as bilirubin, as well as bile salts can inhibit PCR in samples containing feces. In addition, many of the reagents used to cultivate microorganisms or to prepare samples for PCR can inhibit amplification when present at contaminating levels including Triton, Sodium Dodecyl Sulfate (SDS) and others.

Furthermore, host cells (i.e., cells naturally present in the sample being tested for the presence of contaminating microbial cells e.g., a patient's red blood cells and white blood cells) in biological samples tested for the presence of microbial cells contribute to the "dilution" of microbial cells nucleic acids and leads to a decrease in sensitivity of the diagnostic assay. Hence, it would be advantageous to separate and remove as much host's cells as possible in the biological sample while maintaining the microbial cells integrity to increase the sensitivity of nucleic acid testing.

Attempts have been made to remove amplification inhibitors (e.g., host cells, etc.) introduced by conventional whole blood processing methods either by 1) isolating the nucleic acids from the sample prior to nucleic acid analysis; or 2) diluting the processed sample to reduce the effect of inhibitors. Some conventional protocols for nucleic acid analysis of whole blood rely on initial volumes of sample as small as 2-100 μl to reduce inhibitors to an acceptable level. Isolation of nucleic acids is cumbersome and requires that a high concentration of nucleic acid be present to be effective. Dilution or use of small sample volumes significantly compromises the sensitivity of the nucleic acid analysis.

For example, WO 2009/015484 describes a method for isolating microorganisms and/or microorganisms' nucleic acids from bodily fluids comprising treating the sample with a filtered and autoclaved Saponin solution at a concentration between 20 and 100 mg/ml. The method involves the separation of host cells from microbial cells prior to nucleic acid extraction.

EP 0 745 849 describes a method which eliminates inhibitors that interfere in particular with enzymatic nucleic acid reactions and which is also compatible with conventional culturing techniques. Selective lysis of red blood cells is achieved with Triton or Saponin at a final concentration between 0.1 and 0.2%, followed by centrifugation at 5,000-15,000×g for 5-30 min. and subsequent washings to remove inhibitors present in whole blood or introduced by reagents used in the sample processing protocol. The sample volume that may be processed using this method is up to 5 ml. Although this method constitutes an improvement over the previous methods it still requires multiple fold dilution of the initial volume of sample as well as high speed centrifugation. Hence the use of concentrating processing steps is required to obtain sufficiently concentrated nucleic acids for further analysis. In addition, Saponin is a chemically complex substance made of various chemical compounds and Applicants have observed that it is prone to lot-to-lot variability which reduces reproducibility. Moreover, at concentrations employed, Saponins do not lyse white blood cells such as macrophages, thereby contributing to the "dilution" of microbial cells which often results in a decrease in sensitivity.

Some commercially available products for purifying nucleic acids from bodily fluids involve the simultaneous lysis of red and white blood cells as well as microbial cells (SeptiFast™ prep kit from Roche Diagnostics; IsoQuick™ nucleic acid extraction kit from ISC BioExpress; and Nuclisens™ easyMAG™ system from Biomerieux). A disadvantage of this approach is the presence of a larger proportion of blood cells nucleic acids than of microbial nucleic acids which reduces sensitivity of microbial detection in the sample. In addition, systems like SeptiFast™ prep kit require numerous handling steps and take about two hours of treatment prior to extraction of human and microbial DNA. Furthermore it was shown that a majority of blood samples collected from septicemic patients may contain as low as 10 colony Forming Unit (CFU) of microbial cells/ml of blood (Johnson et al., 1993, APMIS, 101:595-601), which may be insufficient to allow detection using these processing methods. For example, the analytical sensitivity of the SeptiFast™ prep kit is approximately 30 CFU of microbe/nil of blood which is well over the concentration of microbe observed in some septicemic patient.

Accordingly, the ideal sample processing method for purification and isolation of microbial cells from biological samples and subsequent release of nucleic acids for nucleic acid testing would include the following features: 1) removes amplification and detection inhibitors, in particular those introduced by lysis of the hosts cells (e.g., red blood cells); 2) releases a sufficient amount of nucleic acids from the microorganisms for amplification; 3) enable the processing of large sample volumes to improve detection sensitivity; 4) uses a single protocol, that allows for the recovery of viable and intact microbial cells which can subsequently be cultured for biochemical testing; and 5) is simple, rapid and requires a limited number of processing steps to reduce possible cross contamination and the time before which a diagnostic is available.

The present description refers to a number of documents, the content of which is herein incorporated by reference in their entirety.

SUMMARY OF THE INVENTION

The present invention relates to a method which advantageously allows the processing of large volumes of biological samples such as whole blood. Unlike previous methods, in which the sample volume that could be analyzed was often limited by the presence of inhibitors (especially in the case of blood), significantly larger volumes may be processed and nucleic acids from microorganisms reproducibly amplified by the method of the present invention. The ability to amplify from large sample volumes using fewer processing steps allows the practitioner to detect more rapidly rare target sequences which may be missed when a small aliquot of a sample or a diluted sample must be amplified to avoid interference from inhibitors.

This method is compatible with both conventional culturing techniques and nucleic acid analysis allowing a single biological sample to be processed for both uses without the need to separate sample processing protocols. The method is based on the discovery of reagents and procedures which can be used to selectively lyse the hosts (subject's) cells (e.g., red blood cells and white blood cells) without substantial lysis of the cells of the microorganisms to be detected in the biological sample. Nucleic acids from microorganisms are protected within the cell and can be separated from the lysed host cells (e.g., present in the supernatant following centrifugation) for further sample processing. The nucleic acids are then released for subsequent analysis.

The method may advantageously employ a single centrifugation step (e.g., between about 3200 g and about 10000 g) to concentrate microorganisms, as opposed to multiple centrifugations/washings. In addition, the method of the present invention may comprise the addition of a small volume of differential lysis solution to the initial volume of biological sample thereby avoiding multiple fold dilution of the sample and the need for additional concentrating steps or the use of smaller sample volumes. Advantageously, no specialized equipment is required to practice the present invention. The reagents are inexpensive and readily available, and none require special handling.

More specifically, in accordance with the present invention, there is provided a method for processing a biological sample for nucleic acid analysis of microorganisms comprising: i) adding to an initial volume of said biological sample a differential cell lysis solution to obtain a final concentration of 0.1 to 1% of SDS in said sample; ii) mixing the solution obtained in step i) for a period of time sufficient to lyse the host cells present in the biological sample, while preserving the integrity of microbial cells; and iii) separating the microbial cells from the lysed host cells components.

In an embodiment, step iii) consists of a single centrifugation, followed by removal of the supernatant and resuspension of microbial cells.

In an embodiment, the resuspension of microbial cells is done in about 1/10 to 1/100 of the initial volume of biological sample.

In an embodiment, the microbial cells are resuspended in a solution consisting essentially of water, saline, culture medium or a buffer compatible with nucleic acid extraction and analysis.

In an embodiment, the above described centrifugation is performed at between about 3200 g and 10 000 g. In a particular embodiment the centrifugation is performed at about 10 000 g. In another embodiment, the centrifugation is performed at about 3200 g for about 3 to about 7 minutes.

In an embodiment the mixing in step ii) of the above described method consists of mixing the solution between about 150 and about 200 rpm. In an embodiment, the mixing is performed for at least about 3 minutes. In a preferred embodiment, the mixing is performed for at least about 5 minutes. In another preferred embodiment, the mixing is performed at about 170 rpm for about 5 minutes.

In an embodiment, of the above-described method further comprises adding glass beads. The glass beads may be added at any step between step i) and step iii). The glass beads may also be added to the microbial cells once the host cells have been separated from the microbial cells (i.e., at the end of step iii). Preferably, the glass beads are added in step i). Preferably, the glass beads consists of a combination of large glass beads ranging from about 710 to about 1180 μm in diameter and of small glass beads ranging from about 150 to about 212 μm in diameter. In an embodiment, the amount of glass beads consists of 3-5 fold the standard combination of small and large glass beads (standard combination is 40 mg+/−20% of beads ranging from 150 to 212 μm and 15 mg+/−35% of beads ranging from 710 to 1180 μm in diameter-See Ruclanap™ U.S. Pat. No. 7,494,771).

In an embodiment, the method of the present invention further comprises step iv) consisting of lysing microbial cells to release their nucleic acids in solution. In an embodiment, step iv) involves mechanical lysis of microbial cells. In an embodiment, mechanical lysis is performed by vortexing the microbial cells.

In an embodiment, the method of the present invention further comprises heating the microbial cells following their lysis. In an embodiment, the heating is performed at about 95° C. for at least about 5 minutes.

In an embodiment, the method of the present invention further comprises step v) comprising purifying nucleic acids released from the microbial cells. In an embodiment, the nucleic acids are purified using magnetic beads.

In another embodiment, step iv) involves enzymatic digestion of microbial cells. In an embodiment, the lysis is performed using Achromopeptidase.

In an embodiment of the method of the present invention, the biological sample is a blood sample. In a particular embodiment, the biological sample is a whole blood sample. In a particular embodiment, the blood sample comprises an anticoagulant.

In a related aspect, the method of the present invention may further comprises in step i) adding an anticoagulant. In a particular embodiment, the anticoagulant is EDTA.

In another embodiment of the method of the present invention, step i) further comprises adding an antifoaming agent. In an embodiment, the antifoaming agent is silicone.

In an embodiment, the initial volume of biological sample used in accordance with the method of the present invention is between about 3 and about 10 ml. In an embodiment, the initial volume of biological sample is larger than 3 ml.

In an embodiment, the method of the present invention further comprises culturing a fraction of the microbial cells.

In another embodiment, the method of the present invention further comprises amplifying a target nucleic acid sequence present in the microbial cells.

In a particular embodiment, the differential cell lysis solution consists essentially of SDS in water or saline. In a further embodiment, the differential cell lysis solution comprises 1 to 20% SDS, preferably 10% SDS.

In a specific embodiment, the method of the present invention consists essentially of the steps described above (i.e., that it does not include undisclosed additional steps that would significantly modify the method of the present invention).

In a preferred embodiment, the final concentration of SDS once the differential lysis solution has been added is between about 0.4% and about 0.75% (e.g., 0.4, 0.45, 0.5, 0.55, 0.6, 0.65, 0.7, 0.75). In a particular embodiment, the final concentration of SDS is between about 0.4% and about 0.5%. In a particularly preferred embodiment, the final concentration of SDS is about 0.5% SDS. In yet another aspect, the final concentration of SDS once the differential cell lysis solution has been added is between about 0.1% to 1% SDS.

In an embodiment the above-described method further comprises the use of an automated system such as the BD MAX™ System for iv) lysing microbial cells; v) isolating and purifying microbial nucleic acids; vi) performing amplification and detection of microbial nucleic acids; or vii) any combinations of iv) to vi).

In a related aspect, the present invention concerns a kit for practicing the above described method of the present invention.

In an embodiment, the kit of the present invention comprises i) a differential cell lysis solution comprising SDS as a lysing agent and at least one of: ii) one or more reagents for microbial nucleic acid extraction; iii) one or more reagents for microbial nucleic acid purification; iv) one or more reagents for microbial cell or microbial nucleic acid detection; v) an anticoagulant; vi) an antifoaming agent; and vii) instructions for practicing the method of the present invention. In an embodiment, the kit comprises at least two of ii) to vii). In an embodiment, the kit comprises at least three of ii) to vii). In an embodiment, the kit comprises at least four of ii) to vii). In an embodiment, the kit comprises at least five of ii) to vii).

In an embodiment the kit further comprises a biological sample collection tube. In an embodiment, the kit comprises a combination of glass beads for microbial nucleic acid extraction. In an embodiment, the combination of glass beads consists of a combination of large glass beads ranging from about 710 to about 1180 µm in diameter and of small glass beads ranging from about 150 to about 212 µm in diameter. In a further embodiment, the combination of glass beads consists of 3-5 fold the standard combination of small and large glass beads (standard combination is 40 mg+/−20% of beads ranging from 150 to 212 µm and 15 mg+/−35% of beads ranging from 710 to 1180 µm in diameter—See Ruclanap U.S. Pat. No. 7,494,771).

In an embodiment, the one or more reagents for microbial nucleic acid extraction comprise Achromopeptidase. In an embodiment, the one or more reagents for microbial nucleic acid purification comprise magnetic beads. In an embodiment, the kit comprises EDTA as an anticoagulant.

In an embodiment, the kit comprises one or more oligonucleotides for detecting the presence of one or more microbial nucleic acids. In an embodiment, the kit further comprises reagents for nucleic acid amplification. In an embodiment, the kit comprises one or more reagents for microbial cell culture.

In yet another aspect, the present invention provides a differential cell lysis solution consisting essentially of water and about 1% to 20% SDS, preferably, 10% SDS.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
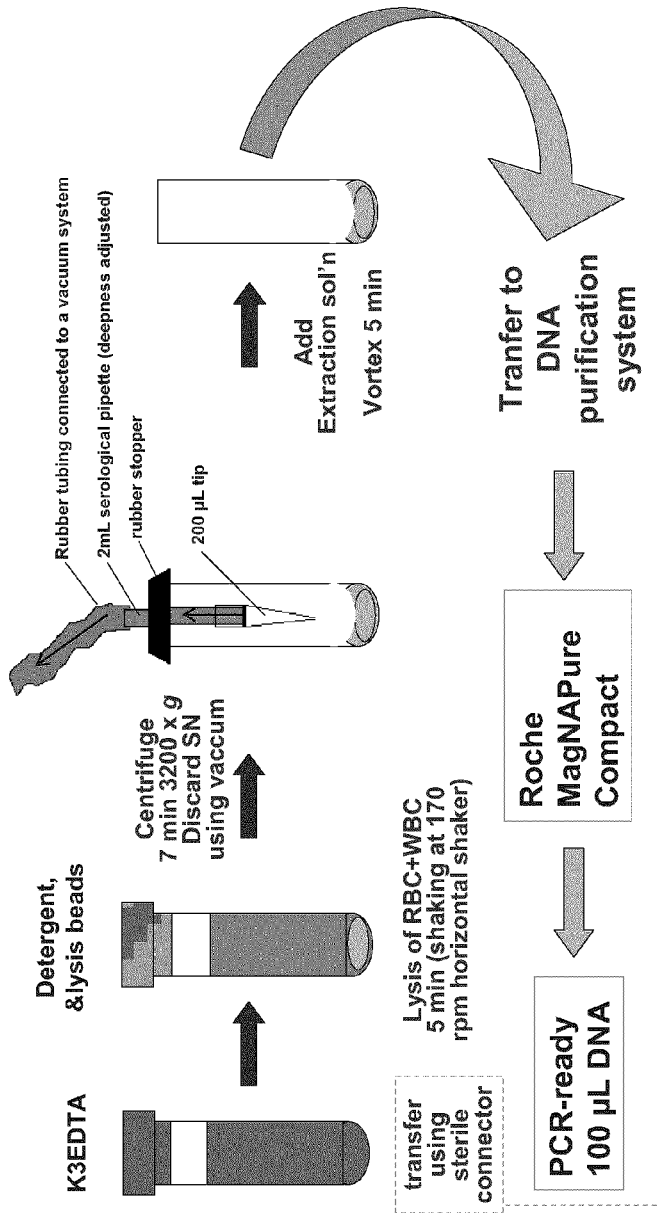
FIG. 1 is a schematic representation of an embodiment of the sample preparation method for 10 mL blood samples.

In order to provide a clear and consistent understanding of the terms used in the present disclosure, a number of definitions are provided below. Furthermore, unless advised otherwise, all technical and scientific terms as use herein have the same meaning as commonly understood to one of ordinary skill in the art to which the present invention concerns.

Throughout this application, the term "about" is used to indicate that a value includes the standard deviation of error for the device or method being employed to determine the value. This may generally include variations between 1-10%.

The use of the word "a" "an" and "the" when used in conjunction with the term "comprising" in the claims and/or the specification may mean "one" but it is also consistent with the meaning of "one or more", "at least one", and "one or more than one".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps and are used interchangeably with, the phrases "including but not limited to" and "comprising but not limited to".

As used herein, the "final concentration" in respect of the SDS relates to the SDS concentration once mixed with a sample, for example, once mixed (contacted) with a biological sample. In the case where additional reagents are added to the sample (e.g., an antifoaming agent, an anticoagulant, glass beads etc.), the final concentration of SDS is with respect to the final volume of the sample during differential lysis (i.e., considering the final volume of the sample, once these additional reagents have been added). Of course, SDS may be added before or after these additional agents but the final concentration must be with respect to the final volume of sample during cell lysis. It is to be understood that any specified range or group is a shorthand way of referring to each and every member of a range or group individually as well as each and every possible subranges or sub-groups encompassed therein and similarly with respect to any sub-ranges or sub-groups therein. The present invention relate and specifically incorporates each and every specific member and combination of sub-ranges or sub-groups therein whatsoever. Thus, for example, when it is said that a final concentration of SDS is between 0.1 and 1%, the final concentration of SDS may be 0.1, 0.11, 0.12, 0.13, 0.14. 0.15, 0.16, 0.17, 0.18, 0.19 or 0.2, 0.3, 0.35, 0.4, 0.45, 0.5, 0.55, 0.6, 0.5, 0.7, 0.75, 0.8, 0.85, 0.9, 0.95 and 1% for example.

As used herein, the term "biological sample" includes but is not limited to, blood (whole blood and fractions thereof (e.g., blood platelets in plasma, plasma, serum), amniotic fluid, aqueous humor, bile, bladder washings, breast exudate, bronchioalveolor washings, cerebrospinal fluid, chyle, chyme, feces, interstitial fluid, lymph, menses, mucus, pleural fluid, pus, saliva, sebum, semen, sputum, sweat, synovial fluid, tears, urine and/or vitreous humor. In a preferred embodiment of the present invention, the biological sample is blood. In an embodiment, the biological sample is obtained from a mammal such as a human.

As used herein the expression "whole blood" is meant to refer to blood with all its components intact (i.e., plasma and platelets have not been removed) that has been withdrawn from a subject. The "whole blood" sample may advantageously already include an anticoagulant such as EDTA to avoid formation of blood clot.

As used herein, the term "subject" or "host" refers to any animal of interest in which it is desired to determine the presence or absence of one or more microorganisms. Non-limiting examples include mice, rats, pigs, cows, pets (e.g., cats, dogs, etc.) rabbits, horses, goats, etc. Preferably, the animal is a mammal, more preferably a human.

According to the present invention "amplification inhibitor" and "detection inhibitor" include any substance that impedes or prevents amplification or detection of a target nucleic acid sequence. In one aspect, isolated microorganisms and/or microorganisms nucleic acids according to the method of the present invention are substantially free of amplification and/or detection inhibitors. Non-limiting examples of amplification and detection inhibitors include proteins (e.g., immunoglobulins), lipids, polysaccharides, heme and heme derivatives (e.g., hemin, hematin, hematoporphyrin, porphyrin derivatives), bile salts and other cell derived substances (e.g., hormones, quercetin etc.), organic and inorganic compounds used for nucleic acid preparation.

As used herein, the expression "target sequence" or "target nucleic acid sequence" denotes a nucleic acid of interest which is generally used to determine the presence or absence of given microorganism(s) in a sample. A "specific target sequence" will enable the detection of a particular microorganism species, genus, family or group while avoiding the unwanted detection of related microbial cells. Preferably, the microorganisms are bacteria.

As used herein, the term "lysis" in connection with cells, generally means any process that leads to the disruption of the outer structure of the cells and its organelles. Cell lysis leads to the breakdown of the intact cell and release of the nucleic acid from the respective cellular compartments or organelles. (e.g., cell nucleus and mitochondria). DNA in eukaryotic cells is separated from the surrounding medium by at least the nuclear envelope and the cytoplasmic membrane. In bacteria, which do not have a nucleus, the nucleic acids are separated from the surrounding medium by a cytoplasmic membrane and a peptidoglycan cell wall and possibly a lipopolysacharide layer. In both eukaryotic and prokaryotic cells, cell lysis leads to cell death.

As used herein, the terms "differential cell lysis" refers to the selective lysis of host cells (all or a fraction thereof) present in a biological sample while maintaining microbial cells integrity.

As used herein, the expressions "microorganisms", "microbial cells" and "microbes" are used interchangeably throughout the specification and include bacteria, yeast, fungi or any combinations thereof. The microorganisms/microbial cells of the present invention may be aerobic or anaerobic. In an exemplary embodiment, microorganisms may cause infections such as bloodstream infections. Microorganisms of the present invention may also be sepsis-causing microorganisms, that is, microorganisms such as bacteria, yeast, and/or fungi that lead to a systemic inflammatory response syndrome (SIRS). Microorganisms that may be purified in accordance with the present invention include those listed in the Rosetta stone microbial database, which is incorporated herein by reference in its entirety: http://www.biomedcentral.com/1471-2180/5/19.

Microorganisms genera of the present invention include, but are not limited to, the *Acinetobacter* genus, *Bacteroides* genus, *Burkholderia* genus, *Capnocytophaga* genus, *Clostridium* genus, *Corynebacterium* genus, *Citrobacter* genus, *Enterobacter* genus, *Enterococcus* genus, *Escherichia* genus, *Haemophilus* genus, *Klebsiella* genus, *Proteus* genus, *Pseudomonas* genus, *Serratia* genus, *Staphylococcus* genus, *Stenotrophomonas* genus, *Streptococcus* genus, *Aspergillus* genus and/or *Candida* genus.

Exemplary microorganisms include but are not limited to: *Abiotrophia adiacens, Abiotrophia defectiva, Achromobacter xylosoxidans* subsp. *denitrificans, Acetobacterium woodi, Acetobacter aceti, Acetobacter altoacetigenes, Acetobacter polyoxogenes, Acholeplasma laidlawii, Acidothermus cellulolyticus, Acidiphilum facilis, Acinetobacter baumannii, Acinetobacter calcoaceticus, Acinetobacter lwoffii, Actinomyces meyeri, Aerococcus viridans, Aeromonas hydrophila, Aeromonas salmonicida, Agrobacterium radiobacter, Agrobacterium tumefaciens, Alcaligenes faecalis* subsp. *faecalis, Allochromatium vinosum, Anabaena variabilis, Anacystis nidulans, Anaerorhabdus furcosus, Aquifex aeolicus, Aquifex pyrophilus, Arcanobacterium haemolyticum, Archaeoglobus fulgidus, Azotobacter vinelandii, Bacillus anthracis, Bacillus cereus, Bacillus firmus, Bacillus halodurans, Bacillus megaterium, Bacillus mycoides, Bacil-* lus pseudomycoides, Bacillus stearothermophilus, Bacillus subtilis, Bacillus thuringiensis, Bacillus weihenstephanensis, Bacteroides distasonis, Bacteroides fragilis, Bacteroides forsythus, Bacteroides ovatus, Bacteroides vulgatus, Bartonella henselae, Bifidobacterium adolescentis, Bifidobacterium breve, Bifidobacterium dentium, Bifidobacterium longum, Blastochloris viridis, Borrelia burgdorferi, Bordetella pertussis, Bordetella bronchiseptica, Brucella abortus, Brevibacterium linens, Brevibacterium flavum, Brevundimonas diminuta, Buchnera aphidicola, Budvicia aquatica, Burkholderia cepacia, Burkholderia mallei, Burkholderia pseudomallei, Buttiauxella agrestis, Butyrivibrio fibrisolvens, Campylobacter coli, Campylobacter curvus, Campylobacter fetus subsp. fetus, Campylobacter fetus subsp. venerealis, Campylobacter gracilis, Campylobacter jejuni, Campylobacter jejuni subsp. doylei, Campylobacter jejuni subsp. jejuni, Campylobacter lari, Campylobacter rectus, Campylobacter sputorum subsp. sputorum, Campylobacter upsaliensis, Cedecea davisae, Cedecea lapagei, Cedecea neteri, Chlamydia pneumoniae, Chlamydia psittaci, Chlamydia trachomatis, Chlorobium vibrioforme, Chloroflexus aurantiacus, Chryseobacterium meningosepticum, Citrobacter amalonaticus, Citrobacter braakii, Citrobacter farmeri, Citrobacter freundii, Citrobacter koseri, Citrobacter sedlakii, Citrobacter werkmanii, Citrobacter youngae, Clostridium acetobutylicum, Clostridium beijerinckii, Clostridium bifermentans, Clostridium botulinum, Clostridium difficile, Clostridium innocuum, Clostridium histolyticum, Clostridium novyi, Clostridium septicum, Clostridium perfringens, Clostridium ramosum, Clostridium sordellii, Clostridium tedium, Clostridium tetani, Comamonas acidovorans, Corynebacterium accolens, Corynebacterium bovis, Corynebacterium cervicis, Corynebacterium diphtheriae, Corynebacterium flavescens, Corynebacterium genitalium, Corynebacterium glutamicum, Corynebacterium jeikeium, Corynebacterium kutscheri, Corynebacterium minutissimum, Corynebacterium mycetoides, Corynebacterium pseudodiphtheriticum, Corynebacterium pseudo genitalium, Corynebacterium pseudotuberculosis, Corynebacterium renale, Corynebacterium striatum, Corynebacterium ulcerans, Corynebacterium urealyticum, Corynebacterium xerosis, Coxiella burnetii, Cytophaga lytica, Deinococcus radiodurans, Deinonema sp., Edwardsiella hoshinae, Edwardsiella tarda, Ehrlichia canis, Ehrlichia risticii, Eikenella corrodens, Enterobacter aerogenes, Enterobacter agglomerans, Enterobacter amnigenus, Enterobacter asburiae, Enterobacter cancerogenus, Enterobacter cloacae, Enterobacter gergoviae, Enterobacter hormaechei, Enterobacter sakazakii, Enterococcus avium, Enterococcus casseliflavus, Enterococcus cecorum, Enterococcus columbae, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus, Enterococcus saccharolyticus, Enterococcus solitarius, Enterococcus sulfureus, Erwinia amylovora, Erwinia carotovora, Escherichia coli, Escherichia fergusonii, Escherichia hermannii, Escherichia vulneris, Eubacterium lentum, Eubacterium nodatum, Ewingella americana, Francisella tularensis, Frankia alni, Fervidobacterium islandicum, Fibrobacter succinogenes, Flavobacterium ferrigeneum, Flexistipes sinusarabici, Fusobacterium gonidiaformans, Fusobacterium necrophorum subsp. necrophorum, Fusobacterium nudeatum subsp. polymorphum, Gardnerella vaginalis, Gemella haemolysans, Gemella morbillorum, Globicatella sanguis, Gloeobacter violaceus, Gloeothece sp., Gluconobacter oxydans, Haemophilus actinomycetemcomitans, Haemophilus aphrophilus, Haemophilus ducreyi, Haemophilus haemolyticus, Haemophilus influenzae, Haemophilus parahaemolyticus, Haemophilus parainfluenzae, Haemophilus paraphrophilus, Haemophilus segnis, Hafnia alvei, Halobacterium marismortui, Halobacterium salinarum, Haloferax volcanii, Helicobacter pylori, Herpetoshiphon aurantiacus, Kingella kingae, Klebsiella omithinolytica, Klebsiella oxytoca, Klebsiella planticola, Klebsiella pneumoniae subsp. ozaenae, Klebsiella pneumoniae subsp. pneumoniae, Klebsiella pneumoniae subsp. rhinosderomatis, Klebsiella terrigena, Kluyvera ascorbata, Kluyvera cryocrescens, Kluyvera georgiana, Kocuria kristinae, Lactobacillus acidophilus, Lactobacillus garvieae, Lactobacillus paracasei, Lactobacillus casei subsp. casei, Lactococcus garvieae, Lactococcus lactis, Lactococcus lactis subsp. lactis, Leclercia adecarboxylata, Legionella micdadei, Legionella pneumophila subsp. pneumophila, Leminorella grimontii, Leminorella richardii, Leptospira biflexa, Leptospira interrogans, Leuconostoc mesenteroides subsp. dextranicum, Listeria innocua, Listeria ivanovii, Listeria monocytogenes, Listeria seeligeri, Macrococcus caseolyticus, Magnetospirillum magnetotacticum, Megamonas hypermegale, Methanobacterium thermoautotrophicum, Methanococcus jannaschii, Methanococcus vannielii, Methanosarcina barkeri, Methanosarcina jannaschii, Methylobacillus flagellatum, Methylomonas Clara, Micrococcus luteus, Micrococcus lylae, Mitsuokella multacidus, Mobiluncus curtisii subsp. holmesii, Moellerella thermoacetica, Moellerella wisconsensis, Moorella thermoacetica, Moraxella catarrhalis, Moraxella osloensis, Morganella morganii subsp. morganii, Mycobacterium avium, Mycobacterium bovis, Mycobacterium gordonae, Mycobacterium kansasii, Mycobacterium leprae, Mycobacterium terrae, Mycobacterium tuberculosis, Mycoplasma capricolum, Mycoplasma gallisepticum, Mycoplasma genitalium, Mycoplasma hominis, Mycoplasma pirum, Mycoplasma mycoides, Mycoplasma pneumoniae, Mycoplasma pulmonis, Mycoplasma salivarium, Myxococcus xanthus, Neisseria animalis, Neisseria canis, Neisseria cinerea, Neisseria cuniculi, Neisseria elongata subsp. elongata, Neisseria elongata subsp. intermedia, Neisseria flava, Neisseria flavescens, Neisseria gonorrhoeae, Neisseria lactamica, Neisseria meningitidis, Neisseria mucosa, Neisseria perflava, Neisseria pharyngis var. flava, Neisseria polysaccharea, Neisseria sicca, Neisseria subflava, Neisseria weaveri, Obesumbacterium proteus, Ochrobactrum anthropi, Pantoea agglomerans, Pantoea dispersa, Paracoccus denitrificans, Pasteurella multocida, Pectinatus frisingensis, Peptococcus niger, Peptostreptococcus anaerobius, Peptostreptococcus asaccharolyticus, Peptostreptococcus prevotii, Phormidium ectocarpi, Pirellula marina, Planobispora rosea, Plesiomonas shigelloides, Plectonema boryanum, Porphyromonas asaccharolytica, Porphyromonas gingivalis, Pragia fontium, Prevotella buccalis, Prevotella melaninogenica, Prevotella oralis, Prevotella ruminocola, Prochlorothrix hollandica, Propionibacterium acnes, Propionigenium modestum, Proteus mirabilis, Proteus penneri, Proteus vulgaris, Providencia alcalifaciens, Providencia rettgeri, Providencia rustigianii, Providencia stuartii, Pseudomonas aeruginosa, Pseudomonas fluorescens, Pseudomonas putida, Pseudomonas stutzeri, Psychrobacter phenylpyruvicum, Pyrococcus abyssi, Rahnella aquatilis, Rickettsia prowazekii, Rhizobium leguminosarum, Rhizobium phaseoli, Rhodobacter capsulatus, Rhodobacter sphaeroides, Rhodopseudomonas palustris, Rhodospirillum rubrum, Ruminococcus albus, Ruminococcus bromii, Salmonella bongori, Salmonella

*choleraesuis* subsp. *arizonae*, *Salmonella choleraesuis* subsp *choleraesuis*, *Salmonella choleraesuis* subsp. *diarizonae*, *Salmonella choleraesuis* subsp. *houtenae*, *Salmonella choleraesuis* subsp. *indica*, *Salmonella choleraesuis* subsp. *salamae*, *Serpulina hyodysenteriae*, *Serratia ficaria*, *Serratia fonticola*, *Serratia grimesii*, *Serratia liquefaciens*, *Serratia marcescens*, *Serratia odorifera*, *Serratia plymuthica*, *Serratia rubidaea*, *Shewanella putrefaciens*, *Shigella boydii*, *Shigella dysenteriae*, *Shigella flexneri*, *Shigella sonnei*, *Sinorhizobium meliloti*, *Spirochaeta aurantia*, *Staphylococcus aureus*, *Staphylococcus aureus* subsp. *aureus*, *Staphylococcus auricularis*, *Staphylococcus capitis* subsp. *capitis*, *Staphylococcus cohnii* subsp. *cohnii*, *Staphylococcus epidermidis*, *Staphylococcus haemolyticus*, *Staphylococcus hominis*, *Staphylococcus hominis* subsp. *hominis*, *Staphylococcus lugdunensis*, *Staphylococcus saprophyticus*, *Staphylococcus sciuri* subsp. *sciuri*, *Staphylococcus simulans*, *Staphylococcus warneri*, *Stigmatella aurantiaca*, *Stenotrophomonas maltophilia*, *Streptococcus acidominimus*, *Streptococcus agalactiae*, *Streptococcus anginosus*, *Streptococcus bovis*, *Streptococcus cricetus*, *Streptococcus cristatus*, *Streptococcus downei*, *Streptococcus dysgalactiae*, *Streptococcus equi* subsp. *equi*, *Streptococcus ferus*, *Streptococcus gordonii*, *Streptococcus macacae*, *Streptococcus mitis*, *Streptococcus mutans*, *Streptococcus oralis*, *Streptococcus parasanguinis*, *Streptococcus pneumoniae*, *Streptococcus pyogenes*, *Streptococcus ratti*, *Streptococcus salivarius*, *Streptococcus salivarius* subsp. *thermophilus*, *Streptococcus sanguinis*, *Streptococcus sobrinus*, *Streptococcus suis*, *Streptococcus uberis*, *Streptococcus vestibularis*, *Streptomyces anbofaciens*, *Streptomyces aureofaciens*, *Streptomyces cinnamoneus*, *Streptomyces coelicolor*, *Streptomyces collinus*, *Streptomyces lividans*, *Streptomyces netropsis*, *Streptomyces ramocissimus*, *Streptomyces rimosus*, *Streptomyces venezuelae*, *Succinivibrio dextrinosolvens*, *Synechococcus* sp., *Synechocystis* sp., *Tatumella ptyseos*, *Taxeobacter occealus*, *Tetragenococcus halophilus*, *Thermoplasma acidophilum*, *Thermotoga maritima*, *Thermus aquaticus*, *Thermus thermophilus*, *Thiobacillus ferrooxidans*, *Thiomonas cuprina*, *Trabulsiella guamensis*, *Treponema pallidum*, *Ureaplasma urealyticum*, *Veillonella parvula*, *Vibrio alginolyticus*, *Vibrio anguillarum*, *Vibrio cholerae*, *Vibrio mimicus*, *Wolinella succinogenes*, *Xanthomonas citri*, *Xanthomonas oryzae*, *Xenorhabdus bovieni*, *Xenorhabdus nematophilus*, *Yersinia bercovieri*, *Yersinia enterocolitica*, *Yersinia frederiksensii*, *Yersinia intermedia*, *Yersinia pestis*, *Yersinia pseudotuberculosis*, *Yersinia rohdei*, *Yokenella regensburgei* and *Zoogloea ramigera*.

The present invention concerns a simple, rapid and efficient method of enriching and isolating microbial cells and their nucleic acids in biological sample. The present method requires fewer manipulative steps and advantageously allows the simple processing of large volumes of sample. Because of the efficiency of the methods of the present invention in concentrating and purifying microorganisms and/or their nucleic acids and to remove inhibitors (amplification and/or detection inhibitors), the sample may be as large as 10 ml. In contrast with prior methods for differential lysis which employ multiple fold dilution of the sample, the method of the present invention employs only the addition of a small volume (e.g., ⅕ to 1/100 of the initial volume of the bodily fluid sample) of a chemically well-defined lysis agent (SDS). The concentration of SDS used allows the selective (differential) lysis of host cells (e.g., red blood cells and white blood cells) while maintaining microbial cells integrity without impeding subsequent nucleic acids analysis.

Preferably, the concentration of SDS used is low enough after nucleic acid purification to avoid any amplification inhibition.

According to the present invention, host cells present in a biological sample include any endogenous cell in a given host, for example a human subject. Host cells present in biological samples include for example red blood cells and white blood cells in blood; bladder cells, kidney cells and prostate cells in urine, epithelial cells in saliva, etc. The term "host cells" and "subject cells" are used herein interchangeably.

In one aspect thereof, the present invention relates to a method for isolating microorganisms and/or microorganisms' nucleic acids from a biological sample that is suspected of comprising microorganisms. The method comprises contacting the biological sample with a concentrated differential cell lysis solution comprising SDS in an amount sufficient to obtain a final concentration of between about 0.1 and about 1% SDS. Preferably, the final concentration of SDS is between about 0.4% and about 0.75% SDS. More preferably, the final concentration of SDS is about 0.5%. In a particular embodiment, the differential cell lysis solution of the present invention consists essentially of SDS in water or saline. The differential cell lysis solution is added to the sample for a period of time sufficient to lyse the host's cells (e.g., red blood cells and white blood cells) contained in the sample, while maintaining microbial cells integrity. It is known that SDS may be inhibitory to amplification of nucleic acids and is incompatible with cell culture. However, it was surprisingly found that at low concentrations between about 0.1 and about 1%, preferably between about 0.4 and about 0.75%, it is extremely efficient in lysing host's cells (e.g., red blood cells and white blood cells), while leaving the microbial cells intact. In addition, under the conditions of the present invention, SDS is not inhibitory to nucleic acid testing when a nucleic acid purification step is performed and is compatible with microbial cell culture. Another advantage of SDS over other lytic reagents such as Saponin, is that it is chemically well-defined and significantly less prone to lot-to-lot variations.

Thus, in accordance with the present invention, the step of contacting the biological sample with a differential cell lysis solution to obtain a final low concentration of SDS between about 0.1% and 1% allows the selective lysis of the host cells (e.g., red blood cells and white blood cells) while maintaining the integrity and viability of the microorganisms present in the sample. In accordance with the present invention the expression "maintaining integrity" in connection with microbial cells means maintaining microbial cells nucleic acids within the microbial cells. For example, in the case of bacteria, the bacterial cell membrane and/or cell wall must be sufficiently intact to keep bacterial nucleic acids within the cell. In accordance with the present invention "viable microorganisms" are organisms that can undergo cell division. "Metabolically active organisms" are microorganisms that can carry metabolic functions but that may not necessarily be able to undergo cellular division (for example, they may be detected by biochemical analysis).

The amount of biological sample used in accordance with the method of the present invention will vary depending on the type of sample that is assessed for the presence of microbial cells. The method of the present invention is particularly useful for large volumes of biological samples. For example 3, 4, 5 or even 10 ml of blood can be conveniently processed without the need for prior concentration or blood cells. This is possible because of the low concentration of SDS required which reduces the initial dilution of the sample by the lytic solution. Thus, in an aspect of the present invention, the biological sample is taken from a subject and then contacted directly with a small volume of an SDS solution (typically less then 1 ml; less then 750 µl, preferably less then 500 µl for a 10 ml sample, i.e., 1/20) to obtain a final concentration of between about 0.1 and about 1% SDS, preferably between about 0.4 and about 0.75% SDS. In an embodiment, the biological sample is taken from the subject and put directly in a container (tube) that contains a suitable amount of an SDS solution of the present invention to 1) minimize the handling/processing steps susceptible to contaminate the sample; and 2) to reduce the processing time for purifying the microorganisms or microbial nucleic acids to be tested.

In addition to the differential cell lysis solution (to obtain a final concentration of 0.1-1% SDS), other reagents may be added to the initial biological sample, depending on the sample's nature and the analysis to be performed.

There are several types of anticoagulants, which differ in their mechanism of action and which need to be selected carefully to avoid problems with certain laboratory applications. Heparin binds to antithrombin III and accelerates the inactivation of thrombin and other clotting factors. EDTA chelates metals, such as calcium and magnesium, which may be beneficial for some blood-based assays but adversely affect others. For example, in the case of a whole blood sample and of amplification assays, an anticoagulating agent such as EDTA or heparin may be added to prevent the formation of blood clots. As an anticoagulant, EDTA is well suited for DNA-based assays but is problematic for cytogenetic analyses. Despite anecdotal accounts of problems in PCR assays, studies have generally found that the use of heparin or EDTA produces equivalent results in PCR assays. EDTA is available in powder form, spray dried or as a liquid solution in a collection tube. Acid citrate dextrose also chelates calcium. Citrate-stabilized blood has been reported to result in better quality RNA and DNA than other anticoagulants (Vaught. Cancer epidemiology, Biomarkers and prevention 2006; 15(9):1582-4).

Optionally, an anti-foaming agent may be added to the biological sample. These agents are chemical additives that help reduce the formation of foam in the sample which can hamper its processing. For example, in the case of blood, the foam formation is thought to occur as a result of the agitation of the blood and air in the presence of albumin present in high concentration in blood. Non-limiting examples of anti-foaming agents include silicone (e.g., Compound A, Dow Coring), Simethicone (Dow) and lecithin. The addition of an antifoaming agent is particularly useful when glass beads are used during the lysis step and blood is the biological sample.

In a particularly advantageous embodiment of the present invention, the hosts cells present in the biological sample are lysed with a solution comprising a combination of a low concentration of SDS as described herein and glass beads. Preferably, the glass beads consist of a combination of small and large glass beads ranging from about 150 to 212 µm in diameter and from about 710 to about 1180 µm in diameter. Large beads may be all of the same size or may be a combination of beads of various sizes within the above noted range. Similarly, small beads may be all of the same size or may be a combination of beads of various sizes within the above noted range. In an embodiment, the amount of glass beads used for a 10 ml sample is about 3 to 5 fold the standard combination of glass beads described in U.S. Pat. No. 7,494,771 (Ruclanap™ method, which is incorporated herein by reference in its entirety). The standard combination of glass beads consists of 40 mg+/−20% of glass beads ranging from about 150 to about 212 µm and 15 mg+/−35% of glass beads ranging from about 710 to about 1180 µm in diameter. Accordingly, in an embodiment, the amount of glass beads used in accordance with the present invention ranges from 120 to 200 mg+/−20% of glass beads ranging from 150 to about 212 µm and 45 to 75 mg+/−35% of glass beads ranging from about 710 to about 1180 µm in diameter for a volume of 10 ml of biological sample (e.g., whole blood). It was discovered that the glass beads advantageously increase the efficiency of lysis of the host cells and increase the yield of purified microorganisms. Without being bound to any particular theory, it is believed that the addition of glass beads increases the efficiency of the method of the present invention by improving the mixing of the sample, by increasing lysis of larger host cells (e.g. white blood cells), by protecting microbial cells in subsequent steps of the sample processing procedure and by improving microorganisms recovery.

Once the differential cell lysis solution is added to the biological sample with, optionally, other reagents such as an antifoaming agent, an anticoagulant and glass beads, the biological sample is mixed at low speed (e.g., on an horizontal shaker between about 150 and about 200 rpm, preferably at about 170 rpm) for a period of time sufficient to lyse the cells present in the biological sample while preserving the microbial cells. The amount of time required is typically about 5 minutes at room temperature. Of course shorter or longer periods of time may be required depending on the type of biological sample to be processed, its volume as well as the type of microbial cells to be lysed and the presence of additional reagents in the sample (e.g., glass beads). One skilled in the art can readily determine the optimal amount of time required for lysing a given biological sample in accordance with the present invention.

Once the host cells are lyzed, microorganisms in the lysed biological sample are concentrated and separated from the lysed host cells. Residual cell debris may also be drawn with the microbial cells. Residual cell debris include residual host cells which are not lysed. For example, in the case of whole blood sample residual cell debris may include a small amount of residual platelets and white blood cells and red blood cells. This residual amount is generally very small as the vast majority of host cells are normally efficiently lysed by the differential cell lysis solution of the present invention. For example, in the case of a whole blood sample, more than 99%, and often more than 99.99% of red blood cells and white blood cells (including macrophages) are lysed by the differential cell lysis solution of the present invention, following mixing at low speed for 5 minutes at room temperature. Hence the differential lysis solution of the present invention is extremely efficient.

Concentration of microbial cells and separation from cell lysis components may preferably be achieved by a single centrifugation for a time sufficient to pellet the microorganisms (e.g., about 5 min. at about 3200-10000 g) using a standard high speed clinical centrifuge. The centrifugation step is preferably performed at room temperature to avoid precipitation of the SDS in solution.

As indicated above, the microorganisms are preferably separated from lysed host cells components using a single centrifugation. Centrifugation in a swinging bucket is preferred because the pellet is then located at the bottom of the tube and can be more easily separated from the supernatant. When centrifugation is used to separate microbial cells from lysed cells components, the supernatant is discarded. The supernatant is preferably removed with minimal disturbance of the pelleted microbial cells. It was found preferable to keep a small amount of supernatant on the surface of the pellet to reduce loss of microbial cells. A vacuum device, designed by the applicant and depicted in FIG. 1, was shown to increase the efficiency of the method by leaving just the right amount of supernatant on the surface of the pellet. In this manner, microorganisms present in the biological sample are concentrated into a significantly reduced sample volume. The pellet is then resuspended in a small volume of water, saline, culture medium or any buffer (e.g., PBS, TE) compatible with the selected method of nucleic acid analysis. One or more washing steps may optionally be performed but it was found to be unnecessary for further efficient culture and amplification of nucleic acids. Thus, depending on the subsequent analysis to be performed one or more washing steps may be used in accordance with the present invention.

The isolated microorganisms may then be further lysed to extract their nucleic acids or cultured in an appropriate medium for further testing. Accordingly, the whole sample or a fraction of it may be used for nucleic acid analysis and/or culturing of the microbial cells. If only nucleic acid analyses are to be performed, the entire pellet comprising the concentrated microbial cells may be used for further extraction of nucleic acids and analysis. Alternatively, a portion of the pellet may be used for culture and a portion for nucleic acid analysis, thereby allowing both procedures to be performed concomitantly and on a single biological sample.

Isolated microorganisms may be lysed to extract and/or purify their nucleic acids by any means known by a person skilled in the art (for example by chemical, enzymatic and/or mechanical lysis). According to a preferred embodiment of the present invention, lysis of the microbial cells is carried out by mechanical methods. Exemplary nucleic acid extraction method is the BD GeneOhm™ Lysis kit. A preferred lysis method is described in U.S. Pat. No. 7,494,771, which uses lysing particles such as glass beads of various diameters to lyse the cells and extract DNA.

As indicated above, the addition of a combination of small and large glass beads together with the SDS solution of the present invention during selective lysis of host cells in the sample, was found to improve selective host cell lysis, to protect microbial cells and to increase recovery of microbial cells. These glass beads, which remain with the microbial cells, may be further used to lyse microbial cells once they have been separated from host cell lysis components by centrifugation. Thus, in a preferred embodiment of the present invention, a combination of small and large glass beads ranging from about 150 to about 212 µm in diameter and from about 710 to about 1180 µm in diameter, respectively are used to mechanically lyse the microbial cells. Preferably, the microorganisms are lysed by resuspending the pellet obtained following centrifugation in a small volume of extraction solution such as Phosphate Buffer Saline (e.g., PBS, 100 µl). The suspension containing the glass beads and microbial cells may then be vortexed at high speed for time sufficient to lyse the microbial cells and release their DNA in solution. Typically, the time required is between about 3-7 minutes. Generally, it was found that vortexing the sample for about 5 minute is sufficient to lyse the microbial cells.

Once the microbial cells have released their DNA in solution, a heating step may advantageously be performed to inactivate amplification inhibitors (e.g., remaining inhibitors such as microbial proteases). Typically, heating the sample at 95° C. for about 5 minutes is sufficient to inactivate the majority of amplification inhibitors. This step is particularly useful in the case where mechanical microbial cell lysis is performed (e.g., using glass beads+vortex). In the event where other cell lysis methods are used, the heating step may not provide any additional advantages.

In an embodiment of the present invention, and preferably in the case where glass beads are not added in the initial differential host cell lysis step, the microbial cells may be lysed and their DNA extracted by any suitable method. For example, enzymatic digestion of microbial cells may be used. As well known in the art, the presence of proteins, lipids, polysaccharides and some other organic or inorganic compounds in the nucleic acid preparation can interfere with nucleic acid analysis methods, especially with polymerase chain reaction (PCR). Thus, the microbial cell lysis method will be selected based on the specific type of nucleic acid analysis subsequently performed (e.g., amplification method, hybridization. etc.) and type of microbial cell to be detected, especially when the released nucleic acids will be used directly, without further purification steps.

Thus, according to a further embodiment of the present invention, the lysis of the microbial cells according to the method of the present invention is carried out enzymatically. Depending on the particular microorganism that is to be detected, an enzyme can be selected that leads to disruption of the cell wall or the outer boundary structure. For example, lysozyme may be used for the lysis of most prokaryotes, lyticase for yeasts, chitinases for fungi, cellulases for algae and proteases for protozoa. Another example is the well-known Achromopeptidase which has potent bacteriolytic activity for gram positive anaerobic and aerobic bacteria including some that are resistant to lysozyme. Of course various combinations of enzymes can be used in accordance with the present invention. Moreover, if for example, bacteria with an unusual cell wall structure are to be lysed, other enzymes may be used according to the method of the present invention, e.g., lysostaphin for dissolving the cell wall of staphylococci. Also, proteases can be used in the lysis of both microbial prokaryotic cells and microbial eukaryotic cells. Of course, the lysis of microbial cells can also be carried out by a method that comprises both mechanical and enzymatic treatments.

In the instance where microbial cells are lysed enzymatically, the buffer in which concentrated microbial cells are resuspended will be the appropriate buffer for optimal enzymatic activity (e.g., Tris 1 mM, EDTA 1 mM, pH 8 for Achromopeptidase). Appropriate lysis buffers for enzymatic disruption are well known in the art. In the case of enzymatic disruption using Achromopeptidase, the pellet comprising microbial cells and residual cell debris is disrupted by reducing the vortexing step to about 1 minute at high speed instead of the about 5 minutes typically used for mechanical disruption using glass beads. Thus, the person skilled in the art will adapt the microbial lysis steps according to the specific method selected.

The microbial nucleic acids in solution may then be directly used for nucleic acid analysis or further concentrated and purified. For example, an aliquot of the lysed microbial cells in solution may directly be used for nucleic acid amplification. Alternatively, the microbial nucleic acids in solution may then be purified by any suitable known method and kits. Preferably, the microbial nucleic acids is purified using solid phase DNA binding agents (e.g., Roche MagNapur™ compact using the Boom et al., technique (magnetic beads); HandyLab™ bead; Qiagen kits, BD MAX™ System, etc.). As well known in the art, some DNA purification techniques can reduce sensitivity of nucleic acid testing by introducing inhibitory substances. For example, the ISOQUICK™ and GNOME™ purification kits result in isolated nucleic acid preparations which are highly inhibitory in amplification reactions. In addition, they can reduce the quality of nucleic acids leading to its shorter storage life. Thus, the nucleic acid extraction method will be selected based on many factors (e.g., type of nucleic acid analysis method including amplification method, type of microbial cell to be detected, etc.). Non-limiting examples of nucleic acid extraction methods include Phenol/Chloroform/isoamyl alcohol extraction, Proteinase K-based methods, Chelex ion exchange resin, silica bead resins or matrices (columns), liquid resins, magnetic beads etc. A preferred method of lysing and/or purifying microbial nucleic acids in accordance with the present invention employs an automated system such as the BD MAX™ System. This system allows to fully automate cell lysis, nucleic acid extraction and/or PCR set-up, amplification and detection.

Once the nucleic acids are purified, the sample may be used for selected nucleic acid analysis or detection protocol. Nucleic acids prepared according to the methods of the present invention are compatible with any of the known nucleic acid analysis and detection protocols, but the methods of the invention have particular advantages (e.g., increased yield, removal of amplification and detection inhibitors, rapidity, etc.) in preparing nucleic acids for use in enzymatic analyses. These include, but are not limited to, restriction digestion and cloning, nucleotide sequencing and nucleic acid amplification. Such protocols are well known in the art and are reviewed in Molecular Cloning: A Laboratory Manual, third Edition, by J. Sambrook, E. F. Fritsch and T. Maniatis, Cold Spring Harbor Laboratory Press, 2001 as well in CSH Protocols, Cold spring harbor laboratory press, www.cshprotocols.org. The present sample processing methods are particularly useful for amplification of nucleic acids because elimination of inhibitors enhances sensitivity of diagnostic tests and allows the practitioner to amplify on a larger amount of microbial DNA because a larger initial volume of biological sample is rapidly processed with a minimum of processing steps further increasing purification yield. Hence, a target sequence which is extremely rare is more likely to be represented in the aliquot of sample amplified, improving the accuracy and reliability of the amplification reaction.

Isolation of microorganisms and microorganisms' nucleic acids according to the method of the present invention may result in 15 to 50 fold concentration of microorganisms and microorganisms' nucleic acids from the biological sample. The microorganisms may be present at high or low concentration in a biological sample. Typically, a microorganism's concentration in a biological sample can be measured by CFU counts which express the number of viable microbial cells per milliliter. An exemplary low concentration of microorganisms in a biological sample is 10 CFU/ml or less. Non-limiting examples include 0.1 to 10 CFU/ml and any range in between or even less. Non-limiting examples of a high microorganism concentration in a biological sample include between 100-10,000 CFU/ml or more. The amount of microbial cells that may be detected in accordance with the method of the present invention is as low as 2.2 CFU/ml and under optimal conditions and depending on the type of microorganism even 1 CFU or less.

Kits

The present invention also provides a kit for concentrating and isolating microorganisms and/or microorganisms' nucleic acids from a biological sample from a subject that is suspected to comprise microorganisms in accordance with the method of the present invention. The kit may comprise a vessel containing a differential lysis solution comprising (or consisting essentially of) about 1% to about 20% SDS, preferably between about 5% and about 15% SDS and even more preferably about 10% SDS, and/or one or more vessels comprising nucleic acid extraction, purification and/or detection reagents. Preferably, the kit may further comprise a combination of glass beads such as the one described in U.S. Pat. No. 7,494,771 (Ruclanap™ method). The amount of glass beads preferably consists of 3-5 fold the standard combination of small and large glass beads (standard combination is 40 mg+/−20% of beads ranging from about 150 to about 212 µm and 15 mg+/−35% of beads ranging from about 710 to about 1180 µm in diameter-See Ruclanap™ U.S. Pat. No. 7,494,771) but other amounts and combinations may be used.

The kit may further comprise other reagents suitable for processing a given biological sample such as an anticoagulant and/or an antifoaming agent. The kit may also optionally comprise a collection tube for collecting the biological sample. The collection tube may already comprise i) an anticoagulant (e.g., EDTA); ii) differential cell lysis solution in accordance with the present invention; iii) antifoaming agent; or iv) any combinations of i) to iii). The kit preferably further comprises instructions for isolating microbial cells and/or microbial nucleic acids from a biological sample. Other reagents may be added according to the type of biological sample to be processed or the microbial cells or microbial nucleic acids to be detected (e.g., suitable bacterial cell culture reagents; primers and/or probes for detecting one or more specific microorganisms, etc.).

The following experimental examples are provided to illustrate certain embodiments of the invention, but are not to be construed as limiting the invention and its equivalents as defined by the appended claims.

Example 1

Material and Methods

Strains, storage and growth conditions. The bacterial species used as a model in the following experiments is *Staphylococcus aureus* (ATCC 36232). The strains were kept cryopreserved in 50% glycerol at −80° C. Bacterial cells were cultured at 35° C. on blood agar plates (Quelab, Montreal). After overnight incubation, three colonies were transferred into 10 mL of Tryptic Soy Broth (TSB) and were incubated overnight and used as stationary phase culture. The number of viable bacteria was determined by the standard spread plate method.

Blood donations. Blood donations were drawn at the Minnesota Memorial Blood Center and kept at 4° C. After usual testing for presence of HBV, HIV, STS and HCV the blood bag was cleared and shipped to INO facility (GSI-Qc) in isolated box cooled with ice packs. Upon reception, the blood was kept at 4° C. until use. Blood donation was 2-4 week-old when tested. The blood bag was dispensed in 50 mL-aliquot into 50-mL Falcon™ tubes and stored at 4° C. An aliquot of 10 mL of blood was tested in blood culture (normal aerobic SA bottle and FA bottle in BacTalert™ 3D) for each bag to detect potential contamination by cultivable bacteria.

Example 2

New Differential Lysis Protocol for Concentrating Microbial Cells from Large Blood Sample Volumes A K3-EDTA fresh blood sample (K3-EDTA used was a liquid EDTA solution) of 5-10 mL was transferred into Sarstedt™ 10 ml tubes with round bottom containing equivalent of three times the lysis matrix contained in IDI-Lysis tube (BD GeneOhm lysis tube cat #441243), 0.1% SDS as blood cell lysing agent and 0.005% of silicone as antifoaming agent. Each tube was then agitated at 170 rpm for 5 min at 25° C. onto a horizontal shaker. Following this blood cell lysis step, blood samples were centrifuged at 3200×g for 7 min. at room temperature.

Supernatant was discarded by aspiration using the device shown in FIG. 1. A small volume of liquid was left over the pellet of microbial cells, cell debris and extraction matrix. A volume of 100 µL of PBS was added before performing lysis of bacteria by vortexing 5 min at high speed on a conventional Vortex Genie™ with multi-tube adaptor. After lysis, the liquid extract was then transferred (approx. 400 µL) to a 2 ml micro tube inserted in the MagNAPure™ Compact (MPC) instrument. DNA purification was done on the MPC instrument using the "DNA Blood 100_400 V3.1" protocol, with an elution volume of 100 µL. The elution buffer from the MagnaPure™ kit was changed to standard TE buffer (10 mM tris pH 8, 1 mM EDTA) as it increased the amount of DNA volume that could be used in PCR (from 3 µl to 17 µl) by decreasing the presence of inhibitory substances in solution. It appears that the buffered water supplied in the kit contained plastic contaminants from the tube in which it is stored into that inhibit PCR.

FIG. 1 summarizes the new protocol for differential lysis and purifying nucleic acids from microorganisms.

Example 3

Comparison of Specimen Processing Performance Between 10 ml and 5 ml Blood Sample Volumes The objective of this experiment was to determine if processing 10 ml of blood samples could yield similar or better results than using 5 ml blood samples. Four experiments were conducted with four different blood donations (E31: 1472658, E34: 1475067, E37: 1477263 and E39: 1482868) according to the general procedure described in Example 1. Blood samples of 5 or 10 mL were spiked at approximately 100 CFU/volume to allow the comparison.

MPC purified DNA was then analyzed by Real-Time PCR, in 96-well plates, on a MyIQ™ (BioRad) instrument. PCR Mastermix™ (MM) was prepared as a 4× solution. S. aureus was amplified using genus specific primer set (TstaG_422 (GGCCGTGTTGAACGTGGTCAAATCA (SEQ ID NO:1)) and TstaG_765 (TIACCATTTCAGTAC-CTTCTGGTAA) (SEQ ID NO:2)) without internal control. Final reaction volume was 25 µL. Sample was added at two volumes (4.7 µL and 18.8 µL) to 6.25 µL of 4×MM with a volume of water to complete to 25 µL in duplicate for each DNA purification. Cycle threshold, endpoint and melt peak height were analyzed.

Figure 2A:
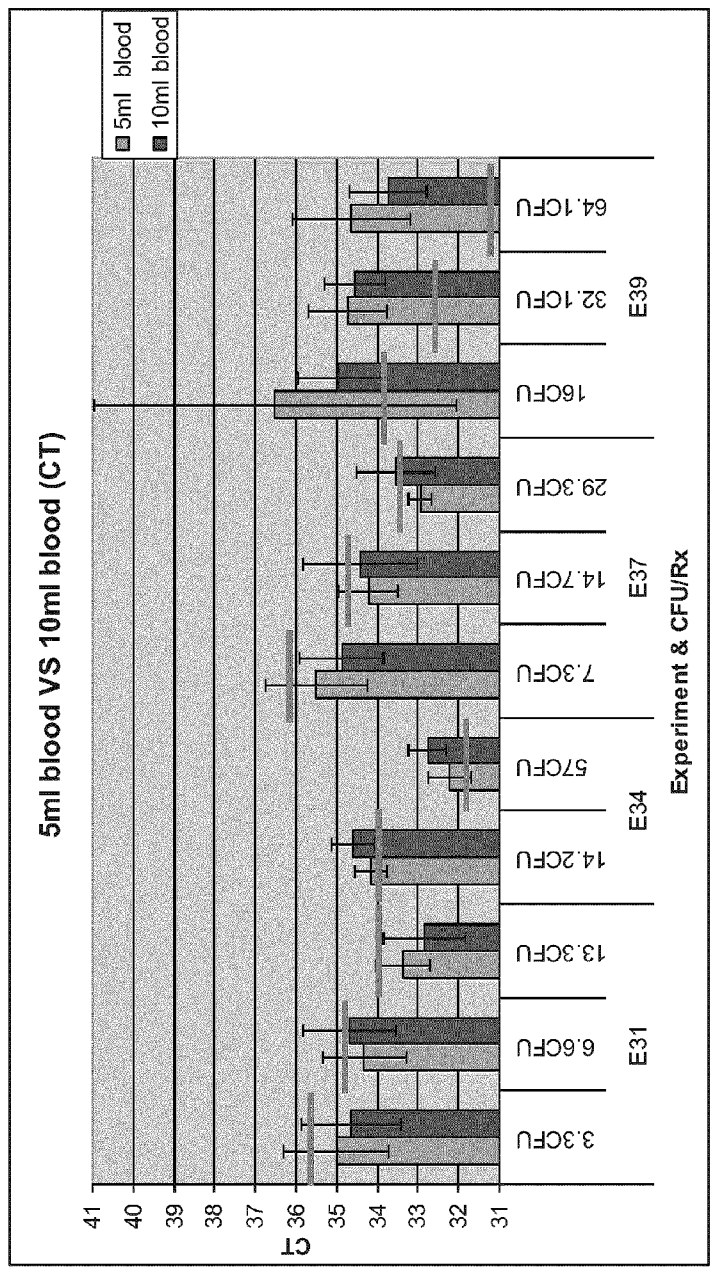
FIG. 2 shows real-time PCR results from sample processing of 5 and 10 mL of blood donations spiked with *S. aureus* at varying CFU loads. Volumes of PCR reagents added for PCR amplification were 4.7 µL, 9.4 µL (except for E34) and 18.8 µL, in 25 µL final PCR volume. Relative CFU/PCR is indicated considering a 100% yield of the entire process. Horizontal red bars indicate reference values for the same DNA loads estimated from a PCR standard curve done with pure DNA. Panel A shows the Cycle Threshold (CT); panel B the End Point (EP) and panel C the Melt peak for various experiments.
Figure 2B:
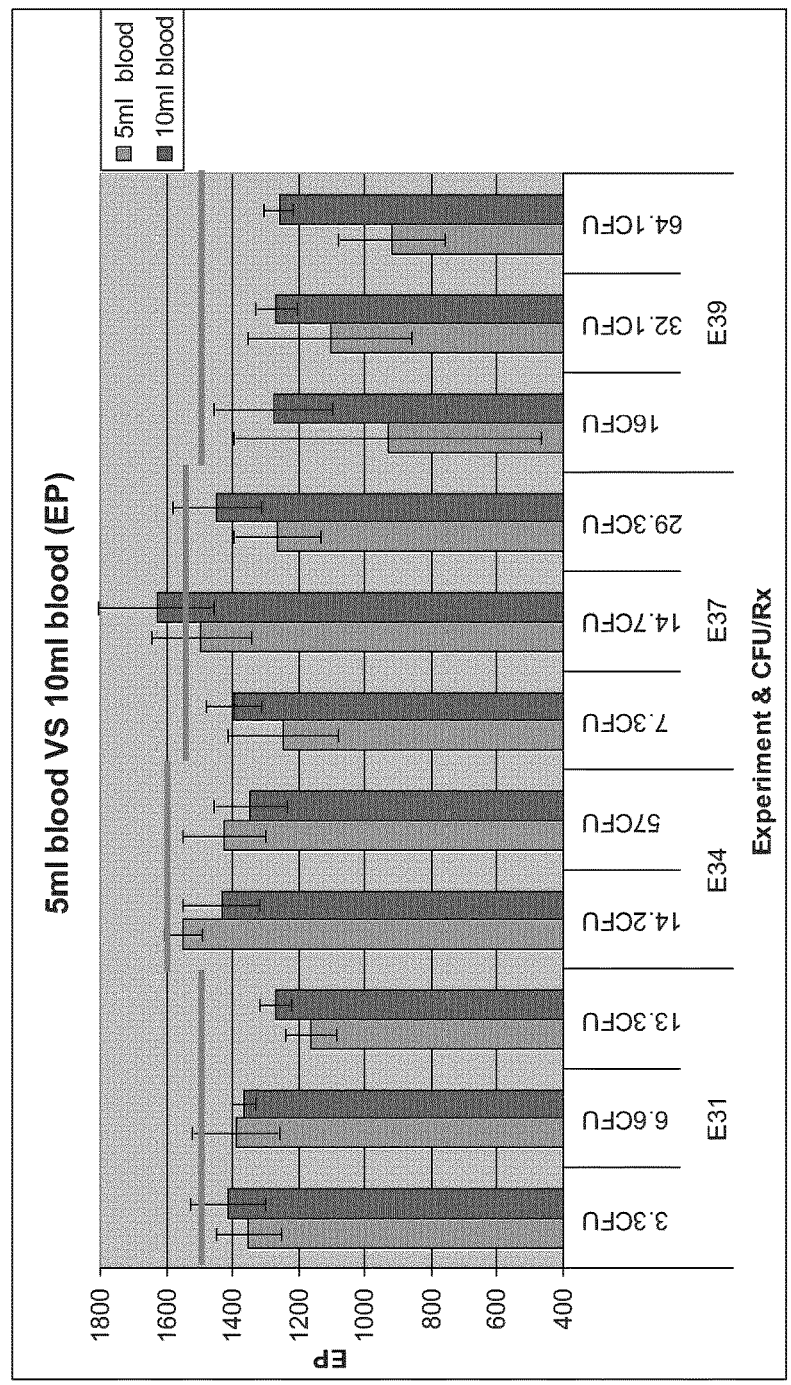
Figure 2C:
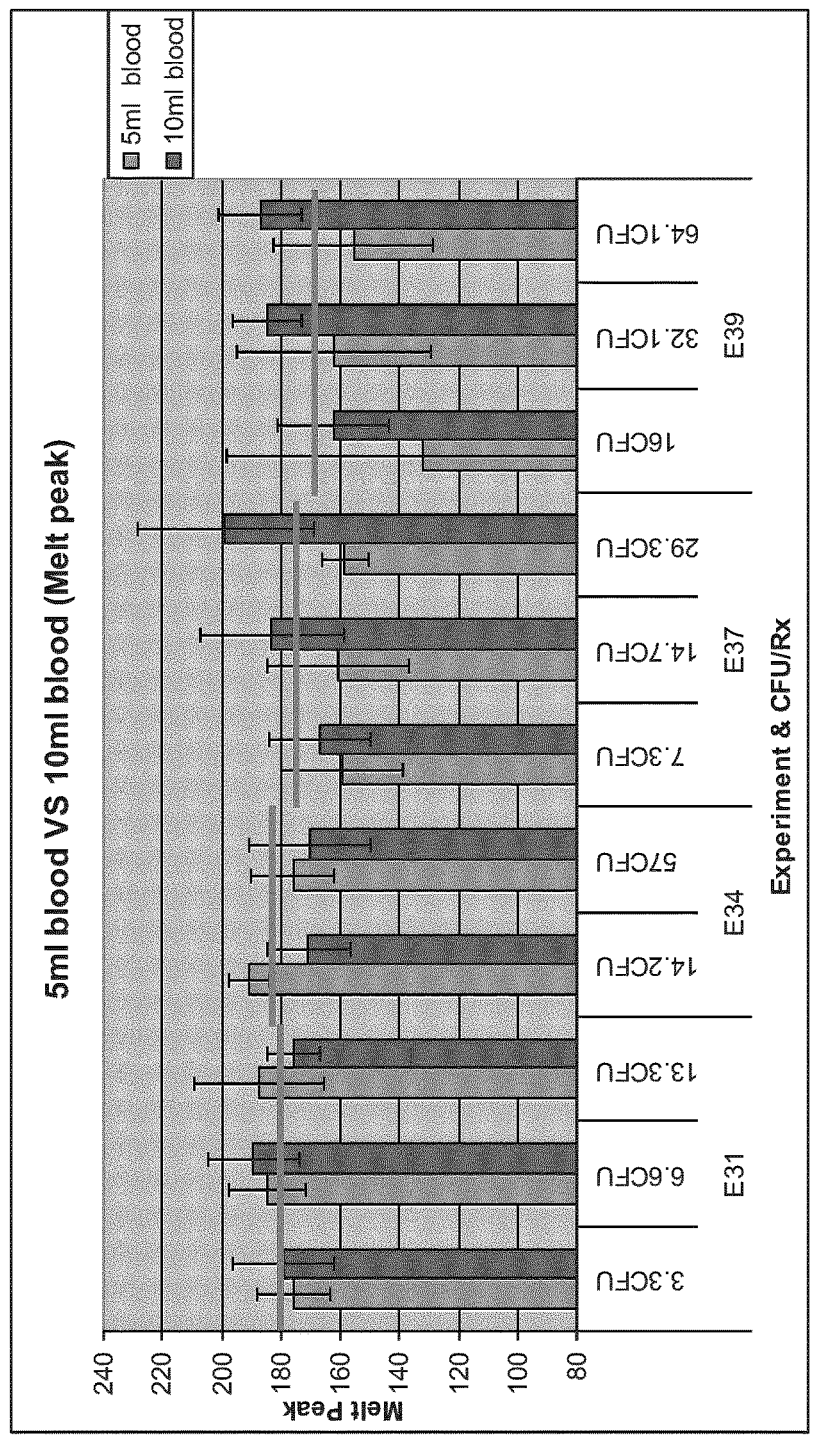

Results. Enumeration of S. aureus inoculum for the various experiments gave respectively 71 CFU (E31), 303 CFU (E34), 156 CFU (E37) 234 and 340 CFU (E39). "Clot error" messages were generated during MPC extractions. All samples with 70 to 340 CFU of S. aureus were detected efficiently with few exceptions (FIG. 2, e.g., 16 CFU samples in E39). CT were not always proportional to initial load. However, CT were reduced as expected by increasing sample volume in PCR. In most cases, CT obtained from blood samples were very similar to those obtained with standard DNA. Experiment E39 led to delayed CT and failure of PCR in lowest sample in PCR. This could be attributable to sample clot that can hamper MPC purification performance (see FIG. 2).

Example 4

Testing of the Differential Lysis Protocol for Concentrating Microbial Cells with 10 ml Fresh Blood Samples Blood donations were used as model system to facilitate feasibility, but the target sample is ultimately fresh blood. Thus, fresh whole blood was collected on K3-EDTA (BD-vacutainer™) and spiked with a mid-log phase culture of S. aureus of approximately 200 CFU/10 ml blood and 40 CFU/10 mL blood (in triplicate). Spiked blood samples were then submitted to differential lysis protocol described in Example 2.

To evaluate lysis efficiency, the highest bacterial load (200 CFU/50 µL in TE buffer) coming from the same culture was loaded into IDI-lysis tube in 2 replicates. This direct extraction allows the elimination of the effects of blood, detergent, antifoam, centrifugation and blood debris on detection performance.

For the spiked IDI-lysis tubes, a step of heating at 95° C. was added to the 5 minutes of vortex to follow the IDI Lysis kit method. After lysis, PBS was added to complete the volume to 400 µL, which was then transferred to a 2 ml micro tube inserted in the MPC. DNA purification was performed on MagNAPure™ with an elution volume of 100 µL. The resulting DNA was named Purified Crude Lysate (PCL). Purified DNAs were then analyzed by Real-Time PCR in duplicate, according to the method of Example 3.

Results.

Figure 3A:
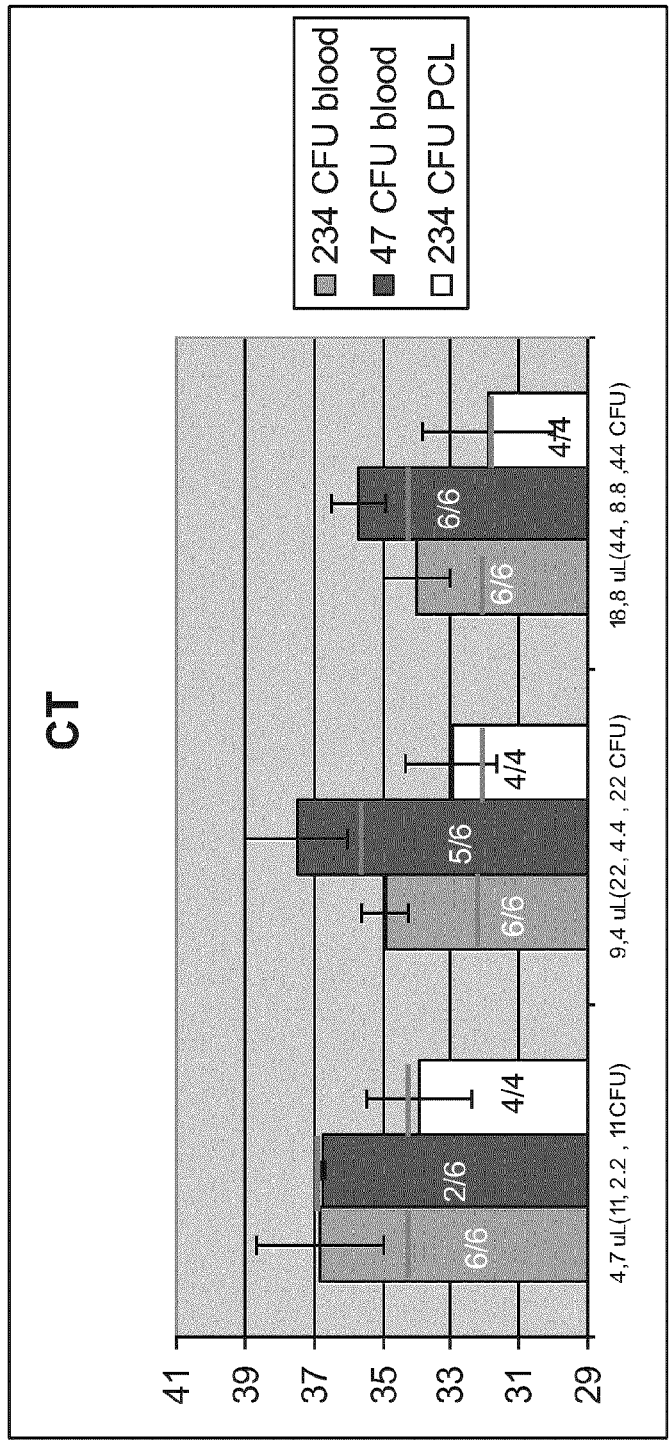
FIG. 3 shows real-time PCR results from sample processing of 10 mL of fresh blood spiked with *S. aureus* at 200 and 40 CFU/10 mL and of CFU directly loaded on IDI Lysis tube (now sold under the name BD GeneOhm™ Lysis kit cat. No. 441243) (PCL). Volumes of PCR reagents added for PCR amplification were 4.7 µL, 9.4 µL and 18.8 µL, in 25 µL final PCR volume. Relative CFU/PCR are given between brackets considering a 100% yield of the entire process. Horizontal red bars indicate reference values for the same DNA loads estimated from a PCR standard curve done with pure DNA. Ratio of #detected/#tested is indicted. Panel A shows the CT; panel B the EP and panel C the Melt peak for various experiments
Figure 3B:
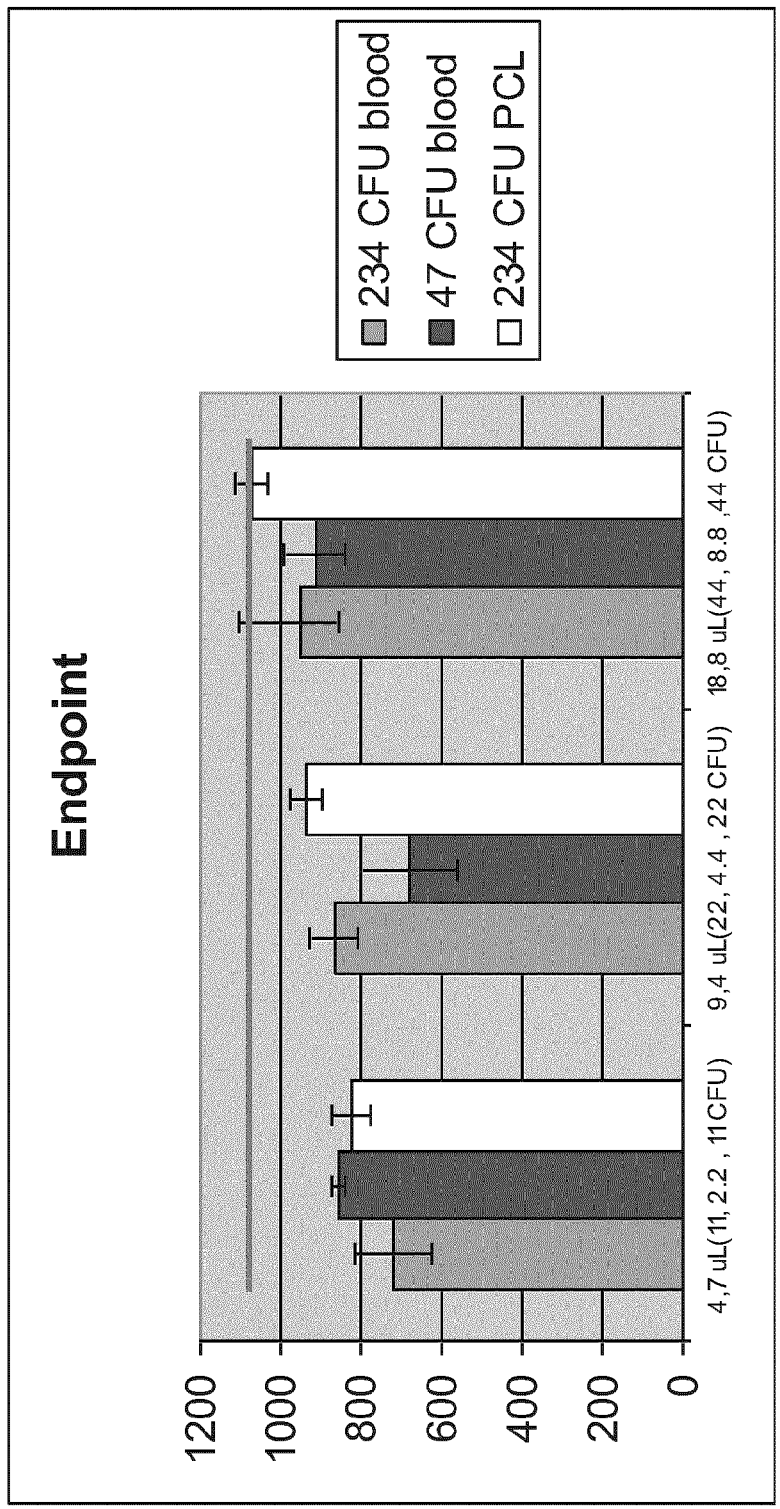
Figure 3C:
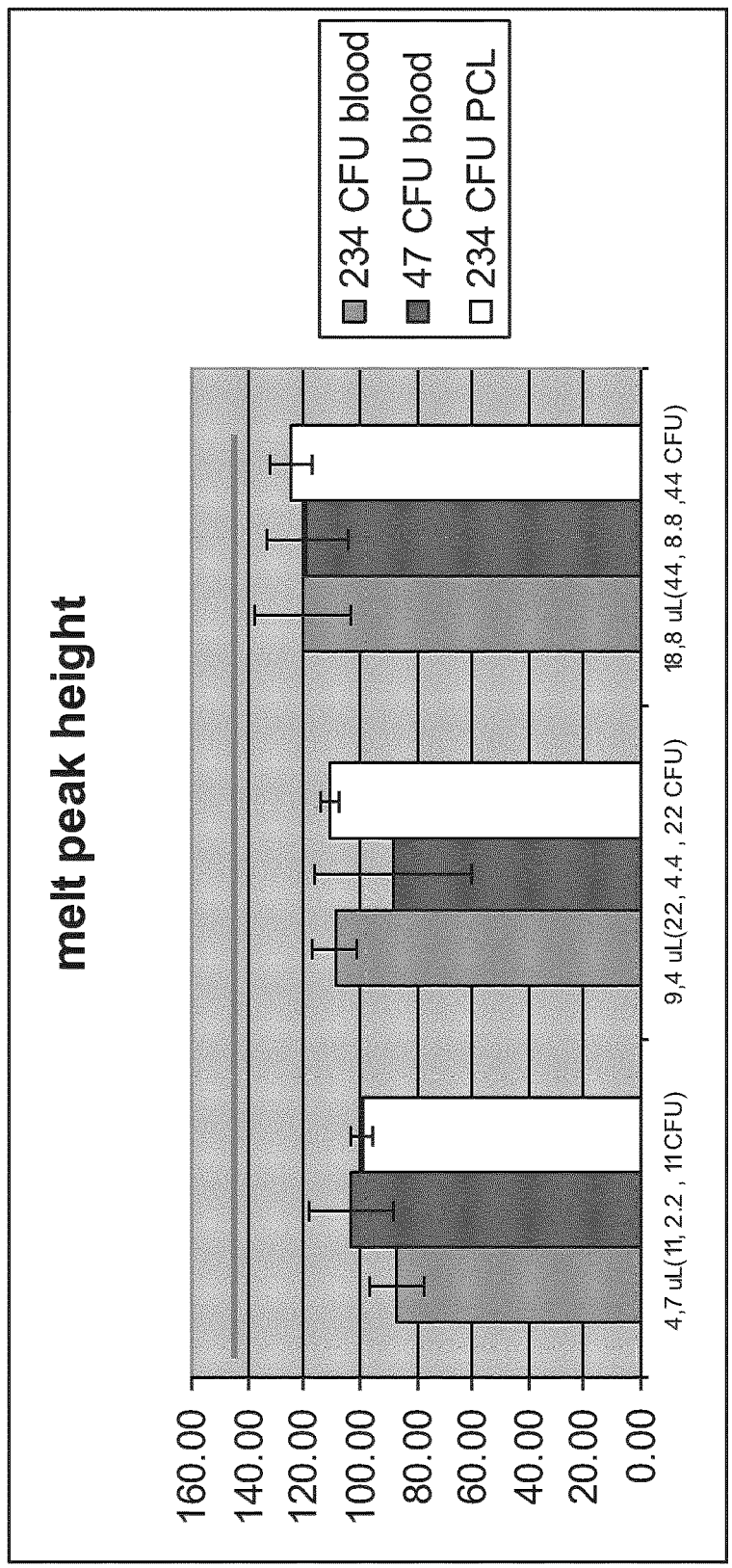

Enumeration of S. aureus inoculums gave respectively 234 and 47 CFU instead of estimated loads of 200 and 40 CFU. PCR results indicate that 47 CFU of S. aureus spiked in 10 mL of whole blood can be efficiently isolated, extracted, DNA purified and detected by PCR (FIG. 3). All replicates (6/6) of the volume of 18.8 µL added to PCR representing the DNA equivalent of 8.8 CFU if a 100% yield is assumed for the entire process, were detected. In addition, 5/6 replicates of the 9.4 µL representing the DNA equivalent of 4.4 CFU, and 2/6 of the 4.7 µL representing the DNA equivalent of 2.2 CFU were detected. The CT mean was significantly higher than the control DNA CT mean, demonstrating slightly variable yield. In addition the EP and Melt peak height of the samples were always lower than the control DNA characteristic of the presence of some residual inhibitors in the samples (FIG. 3).

Comparison of PCR results between sample processing and direct crude lysing showed a difference of 1.5 to 2 cycles, meaning that the sample process yield could be ranged between 25-35%.

Although the present invention has been described hereinabove by way of specific embodiments thereof, it can be modified, without departing from the spirit and nature of the subject invention as defined in the appended claims.

REFERENCES

1. Johnson et al., 1993, APMIS, 101:595-601;
2. White et al., 2006, Clin. Infect. Dis. 42:479-486;
3. Vaught., 2006, Cancer epidemiology, Biomarkers and prevention 15(9):1582-4.

The invention claimed is:

1. A method of preparing a biological sample for nucleic acid analysis of microbial cells comprising:
   i) adding to an initial volume of said biological sample, wherein said initial volume is larger than 3 ml, a differential cell lysis solution to obtain a final concentration of 0.1 to 1% (w/v) of sodium dodecyl sulfate (SDS) in said sample and optionally adding to said initial volume of said biological sample an antifoaming agent and/or an anticoagulant, wherein said biological sample is a blood sample containing host cells and microbial cells and wherein said biological sample is not concentrated prior to addition of said differential cell lysis solution;
   ii) mixing the sample obtained in step i) to lyse the host cells present in the biological sample, while preserving the integrity of microbial cells in the sample; and
   iii) separating the microbial cells from the lysed host cells components, wherein step iii) consists of a single centrifugation, followed by removal of the supernatant and resuspension of microbial cells.

2. The method of claim 1, wherein said resuspension of microbial cells is done in about 1/10 to about 1/100 of the initial volume of biological sample.

3. The method of claim 2, wherein said microbial cells are resuspended in a solution consisting essentially of water, saline, culture medium or a buffer compatible with nucleic acid extraction.

4. The method of claim 3, wherein said centrifugation in step iii) is performed at between about 3200×g and about 10,000×g.

5. The method of claim 1, wherein step i) further comprises adding a combination of large glass beads ranging from about 710 to about 1180 μm in diameter and of small glass beads ranging from about 150 to about 212 μm in diameter, wherein the combination of glass beads consists of 3 to 5 fold the standard combination of glass beads and wherein the standard combination of glass beads is: i) 40 mg+/−20% of beads ranging from about 150 to about 212 μm; and ii) 15 mg+/−35% of beads ranging from about 710 to about 1180 μm.

6. The method of claim 5, further comprising step iv) comprising lysing microbial cells to release their nucleic acids in solution.

7. The method of claim 6, wherein step iv) comprises mechanical lysis of microbial cells.

8. The method of claim 7, wherein said mechanical lysis is performed by vortexing the microbial cells.

9. The method of claim 8, further comprising heating the microbial cells following their lysis.

10. The method of claim 9, further comprising step v) comprising purifying nucleic acids released from the microbial cells.

11. The method of claim 1, wherein said blood sample is a blood sample, comprising an anticoagulant.

12. The method of claim 1, wherein said differential cell lysis solution consists essentially of SDS in water or saline.

13. The method of claim 1, wherein said final concentration of SDS is between about 0.4 and about 0.75% (w/v).

14. The method of claim 1, wherein said final concentration of SDS is between about 0.4 and about 0.5% (w/v).

15. The method of claim 1, wherein step i) comprises adding to said initial volume an antifoaming agent or an anticoagulant.

16. The method of claim 1, wherein step i) comprises adding to said initial volume an antifoaming agent and an anticoagulant.

17. A method of preparing a biological sample for nucleic acid analysis of microbial cells, the method consisting essentially of:
   i) adding to an initial volume of said biological sample, wherein said initial volume is larger than 3 ml, a differential cell lysis solution to obtain a final concentration of 0.1 to 1% (w/v) of sodium dodecyl sulfate (SDS) in said sample and optionally adding to said initial volume of said biological sample an antifoaming agent and/or an anticoagulant, wherein said biological sample is a blood sample containing host cells and microbial cells and wherein said biological sample is not concentrated prior to addition of said differential cell lysis solution;
ii) mixing the sample obtained in step i) to lyse the host cells present in the biological sample, while preserving the integrity of microbial cells in the sample; and
iii) separating the microbial cells from the lysed host cells components, wherein step iii) consists of a single centrifugation, followed by removal of the supernatant and resuspension of microbial cells.

\* \* \* \* \*

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide (Staphylococcus
      aureus)

<400> SEQUENCE: 1
ggccgtgttg aacgtggtca aatca                                              25

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n = inosine

<400> SEQUENCE: 2
tnaccatttc agtaccttct ggtaa                                              25